United States Patent [19]

Huybrechts et al.

[11] Patent Number: 5,739,076
[45] Date of Patent: Apr. 14, 1998

[54] CATALYSTS AND THEIR USE IN OXIDATION OF SATURATED HYDROCARBONS

[75] Inventors: Diane Renata Cornelia Huybrechts, Oud-Turnhout; Philip Luc Buskens, Heverlee; Georges Marie Karel Mathys, Bierbeek; Luc Roger Marc Martens, Meise, all of Belgium

[73] Assignee: Exxon Chemical Patents Inc., Houston, Tex.

[21] Appl. No.: 374,588

[22] PCT Filed: Jul. 23, 1993

[86] PCT No.: PCT/EP93/01972

§ 371 Date: Apr. 19, 1995

§ 102(e) Date: Apr. 19, 1995

[87] PCT Pub. No.: WO94/02245

PCT Pub. Date: Feb. 3, 1994

[30] Foreign Application Priority Data

Jul. 24, 1992 [GB] United Kingdom ............... 9215822
Apr. 16, 1993 [GB] United Kingdom ............... 9307910

[51] Int. Cl.[6] .............................. C07C 55/00; B01J 23/00
[52] U.S. Cl. ...................... 562/512.4; 502/350; 502/351
[58] Field of Search ................... 562/512.4; 502/350, 502/351

[56] References Cited

U.S. PATENT DOCUMENTS 4,490,565  12/1984  Chang et al. ................ 568/798
4,927,525  5/1990   Chu ........................... 208/138
5,412,122  5/1995   Saxton et al. ................ 549/531

FOREIGN PATENT DOCUMENTS

205301 A2  12/1986  European Pat. Off. .

OTHER PUBLICATIONS

Journal of the Chemical Society, vol. 8, May 1992, Camblor et al., "Synthesis of a Titaniumsilicoaluminate Isomorphous to Zeolite Beta and its Application as a Catlayst for the Selective Oxidation of Large Organic Molecules", pp. 589–590.

Manel Dekker Inc. publisher of "Characterization of Heterogenous Catalysts" by Chemical Industries, vol. 15, Chpt. 4, 1984.

Morrison and Boyd, Organic Chemistry, Chapter 19, 3rd Edition, pp. 635 and 11988, 1973.

*Primary Examiner*—Marianne M. Cintins
*Assistant Examiner*—Dwayne C. Jones
*Attorney, Agent, or Firm*—John F. Hunt; John J. Mahon

[57] ABSTRACT

New titanium zeolite Beta catalysts which have been found to be useful as catalysts for the oxidation of organic compounds using organic hydroperoxides as oxidation catalysts. They are particularly useful as ring opening oxidation catalysts and may be used to produce adipic acid from cyclohexane.

11 Claims, 1 Drawing Sheet

CATALYSTS AND THEIR USE IN OXIDATION OF SATURATED HYDROCARBONS

BACKGROUND OF THE INVENTION

The present invention relates to catalyst systems and their use for the oxidation of organic compounds and in particular to the selective oxidation of organic compounds particularly aliphatic compounds and alkyl aromatic compounds. A particularly useful feature is their performance as ring opening catalysts. In a preferred embodiment the invention is concerned with the oxidation of saturated hydrocarbon chains.

Saturated organic compounds are difficult to oxidise and despite attempts to develop methods and techniques for their controlled or selective oxidation techniques using mild conditions with relatively high yields are only known for the conversion of butane via butenes into maleic anhydride. furthermore the known processes use homogenous and sometimes hazardous catalysts requiring complex separation techniques. An example of such processes are given in Catalysis Today Vol. I Nos. 5 of October 1987 relative to the selective catalytic oxidation of butane to maleic anhydride involving dehydrogenation and oxidation of the resulting intermediate olefin, the article in Tetrahedron Vol. 31 pages 777–784 concerning the oxidation of cyclohexane with molecular oxygen and the article in the Journal of the CHEM. SOC. CHEM. COMMUN. 1987 page 1487 and Journal of Molecular Catalysis 44 (1988) pages 73–83. The direct oxidation of saturates to introduce functional groups such as ketones and alcohols using a heterogeneous catalyst system would be extremely attractive.

PCT patent application number GB 8901328 describes the use of catalysts based on crystalline synthetic material comprising silicon and titanium oxides and are characterised by an infra red absorption band at around 950 cm$^{-1}$ to 960 cm$^{-1}$ and typically of the general formula:

$$xTiO_2(1-x)SiO_2$$

where x is from 0.0001 to 0.04 for the oxidation of saturated hydrocarbons.

These catalysts known as TS-1 and TS-2 are typically prepared in the absence of aluminium from a mixture containing a source of silicon oxide, a source of titanium oxide, a nitrogenated organic base and water as described in United Kingdom Patent 2071071 which is concerned with the catalysts themselves or by the dealumination of ZSM-5 and reaction with titanium tetrachloride vapour as described by B. Kraushaar and J. H. C. Van Hoof in Catalysis Letters 1 (1988) pages 81–84. The catalysts may contain small amounts of other metals such as aluminium, gallium and iron (as described in European Patent Application 0226258).

More recently aluminium containing titanium silicalites have been reported for example in EP 0293950 and in Zeolites 12 (1992) 135–137. In this case, the catalysts exhibit both oxidising and acidic catalytic activities.

In EP 0230949 the treatment of TS-1 catalyst with neutralising agents (e.g. alkaline compounds is reported). The examples given in the patent show that TS-1 catalyst treated with alkaline compounds give better yields of epoxides and lower amounts of by-products when they are used as catalysts for the epoxidation of olefins by $H_2O_2$. It is suggested that the applied treatments have a neutralising effect on the catalyst's acidity, and thus prevent the catalyst to initiate undesirable side reactions.

Both TS-1 and TS-2 catalysts contain pores with a diameter of ±5.5 Å. This limits their application to reactions of relatively small substrates, which can easily enter these pores. For example, in paraffin oxidation, n-hexane is oxidized more easily than cyclohexane, and the reactivity of different paraffins decreases with increasing carbon-number and increasing branching. In order to have suitable catalysts for the oxidation of larger organic substrates, the synthesis of larger pore titanium containing zeolites is highly desirable.

Recently, the synthesis of a titanium containing zeolite isomorphous to zeolite Beta has been reported (J. Chem. Soc. Chem. Comm. 1992 (8) 589–590). In the described synthesis method low concentrations of aluminium (Si/Al= 192) are used for the preparation of the synthesis mixture. Like TS-1 and TS-2, the titanium containing zeolite Beta is characterised by an IR absorption at ±960 cm$^{-1}$. It is further reported to catalyse the oxidation with $H_2O_2$ of cyclohexane to cyclohexanol and cyclohexanone and the oxidation of cyclododecane to cyclododecanol, cyclododecanone, cyclododecene and cyclododecadiols. In these reactions the titanium containing zeolite Beta, which has a pore diameter of 7.5 Å, is reported to be more active than the smaller pore TS-1 catalyst.

These catalysts have been reported as oxidation catalysts using aqueous hydrogen peroxide as the oxidising agent. The use of an aqueous system for oxidising organic compounds gives low yields and slow reaction due to the two phase system.

SUMMARY OF THE INVENTION

We have now been able to synthesize a titanium containing zeolite Beta in the presence of higher concentrations of aluminium. Addition of aluminium to the synthesis mixture of zeolite Beta is known to increase the efficiency of the synthesis of the zeolite, as described in Zeolites 8 (1988) p 46–53. We have found that the catalysts can be used for oxidation with organic oxidising agents thus enhancing both yield and rate of the oxidation reaction.

We have also found that the zeolite Beta obtained is not only a more active catalyst but catalyses other oxidation reactions and has different characteristics from previously reported zeolite Beta.

The new method for the synthesis of titanium containing zeolite Beta consists of the preparation of a synthesis mixture containing a source of titanium (e.g. tetraethylorthotitanate), a source of aluminium (e.g. aluminium powder), a source of silicon (e.g. Ludox AS40, 40% colloidal silica) and an organic N-containing base (e.g. tetraethylammoniumhydroxide (TEAOH)), the ageing of this mixture preferably in the presence of hydrogen peroxide during a predefined period, and the hydrothermal treatment of the mixture. The crystals which are formed during the hydrothermal treatment are then isolated from the mother liquor, washed, dried and finally calcined to remove the organic material contained in the structure.

DESCRIPTION OF THE PREFERRED EMBODIMENTS

Typical synthesis mixtures that yield titanium containing zeolite Beta after hydrothermal treatment have the following molar composition

| $SiO_2$ | (0.0001–0.2) $TiO_2$ | (0.005–0.100) $Al_2O_3$ |
|---|---|---|
| | (10–100) $H_2O$ | (0.1–1) TEAOH |

It is preferred that the molar ratio of titanium and silicon to that of aluminium in the synthesis mixture is in the range from 10 to 200.

In a preferred process for making the catalyst, hydrogen peroxide is also present. It is preferred to use the amount of hydrogen peroxide which provides from 10 to 200 moles of hydrogen peroxide per mole of tetraethylorthotitanate (TEOT) when that is used as the source of titanium dioxide.

The new titanium containing zeolite Beta is highly crystalline and is characterized by an IR absorption at ±960 cm$^{-1}$ and by an absorption band in Diffuse Reflectance Spectroscopy at the wave number 47,500 cm$^{-1}$. Diffuse Reflectance Spectroscopy is described in chapter 4 of the book entitled "Characterisation of Heterogeneous Catalysts" by Chemical Industries, Volume 15, published by Manel Dekker Inc. of New York in 1984. The system used was as in FIG. 3 of that chapter using a Cory 5 spectrometer.

The material has been found to be an active oxidation catalyst especially for reactions involving peroxides as oxidant, particularly organic hydroperoxides not previously used with TS-1 or zeolite Beta. The new catalysts are also effective with hydrogen peroxide oxidation. This oxidative catalytic activity is reminiscent of that reported for TS-1 and TS-2, but compared to those two catalysts titanium containing zeolite Beta is more effective in the oxidation of larger substrates, such as cycloparaffins and cycloolefins. Use of these new catalysts with organic hydroperoxides avoids the two phase system with aqueous hydrogen peroxide and thus increases yield.

We have also surprisingly found that when oxidising using hydrogen peroxide the oxidation catalytic performance of titanium containing zeolite Beta irrespective of pore size or aluminium content can be significantly enhanced by treatment of the catalyst with inorganic compounds, preferably acids, bases or ion exchange or by treatment with steam followed by calcination. The treatment is preferably performed before the catalytic reaction is carried out. For example we found that titanium containing zeolite Beta which was treated with a 1.3N HCl solution and calcined, was more active for the oxidation of cyclohexane by $H_2O_2$ than the non treated titanium containing zeolite Beta.

Even more surprisingly, we found that the preferred aluminium and titanium containing zeolite Beta of the present invention either treated or not treated, catalyze (ring opening) cyclic compounds to yield acids. For example, the formation of adipic acid was observed in the oxidation of cyclohexane by tertiary butyl peroxide or $H_2O_2$ catalyzed by titanium containing zeolite Beta as was the oxidation of cyclopentane to glutaric acid. In this reaction, the catalytic behaviour of titanium containing zeolite Beta is strikingly different from that of TS-1. Under comparable reaction condition using hydrogen peroxide, only cyclohexanols and cyclohexanones are formed on TS-1 whereas high selectivity for adipic acid can be obtained using our new titanium Beta. Selectivity may be further increased particularly with $H_2O_2$ oxidation if the catalyst has been treated for ion exchange or steam treatment.

In the oxidation process of this invention the oxidising agent is hydrogen peroxide or an organic hydroperoxide, examples of suitable organic hydroperoxides include di-isopropyl benzene monohydroperoxide, cumene hydroperoxide, tert.butyl hydroperoxide, cyclohexylhydroperoxide, ethylbenzene hydroperoxide, ter.t.amyl hydroperoxide, tetraline hydroperoxide and the compound containing the saturated organic group is liquid or in the dense phase at the conditions used for the reaction. It is also preferred that the reaction is carried out in the presence of a suitable solvent. The use of tertiary butyl hydroperoxide is particularly beneficial since the tertiary butyl alcohol produced can readily be converted to the valuable isobutylene molecule.

The catalyst used in this invention is preferably prepared from a reaction mixture consisting of sources of silicon oxide, titanium oxide a source of aluminum, a nitrogen containing organic base and water.

The silicon oxide source can be a tetraalkylorthosilicate, preferably tetraethylorthosilicate, or simply a silicate in colloidal form.

The titanium oxide source is a hydrolysable titanium compound preferably chosen from $TiOCl_4$, $TiOCl_2$ and $Ti(alkoxy)_4$, preferably $Ti(OC_2H_5)_4$.

The organic base is preferably a tetraalkylammonium hydroxide, and in particular tetraethyl ammonium hydroxide.

In the preferred method to produce the catalyst the mixture of these reactants is subjected to hydrothermal treatment in an autoclave at a temperature of between 130° and 200° C. under its own developed pressure, for a time of 1 hour to 30 days preferably 6 to 30 days until the crystals of the catalyst precursor are formed. These are separated from the mother solution, carefully washed with water and dried.

The precursor crystals are then heated for between 1 and 72 hours in air at 200°–600°, preferably 550° C., preferably during about 20 hours to eliminate the nitrogenated organic base.

The catalyst may also contain alkali metal cations $M^+$ where M is sodium or potassium and in this situation it is preferred that the molar ratio of $M^+:SiO_2$ is in the range 0.001 to 0.5.

It is possible to oxidise saturated aliphatic compounds including aliphatic substituents of aliphatic/aromatic compounds by the process of the invention. The saturated groups which may be oxidised by the process of this invention include long or short, branched or linear alkanes containing 3 or more, preferably 3 to 30, more preferably 3 to 12 carbon atoms, cyclic alkanes and mono- and poly-alkyl aromatics in which at least one of the alkyl groups contain at least two preferably at least three, more preferably 3 to 18, most preferably 3 to 12 carbon atoms and mono- and poly-alkyl cyclic alkanes. The process of the invention is equally applicable to the epoxidation of olefins, dienes, the production of ether glycols, diols, the oxidation of alcohols or ketones, aldehydes, to acids and the hydroxylation of aromatics.

We have surprisingly found that by the selection of appropriate conditions saturated groups may be oxidised with high selectivity to alcohols and ketones under relatively mild conditions. One particularly useful application is in the oxidation of linear and branched paraffins to secondary alcohols and ketones. The process is especially useful in the lower carbon number range to enable use of low-cost propane and butane feedstock in the manufacture of isopropanol alcohol, acetone, secondary butyl alcohol and methyl ethyl ketone. The aliphatic substituent may be a part of a totally aliphatic compound, an aryl compound (alkyl aromatic) or an alkylnaphthene compound. Furthermore, said compound may contain other functional groups providing they do not prevent the desired oxidation reaction taking place.

The reactivity sequence for the aliphatic compounds slows down from tertiary to secondary and to primary compounds.

The oxidising agents used in the reaction may be organic hydroperoxides, ozone, $N_2O$ or hydrogen peroxide, organic hydroperoxides as described being preferred since the yields and reaction rates are higher than with the aqueous hydrogen peroxide system. When aqueous hydrogen peroxide is used the solution contains from 10–100, preferably 10 to 70 wt. % hydrogen peroxide for example diluted hydrogen peroxide (40% by weight in water). It is also preferred that a polar solvent be present when aqueous hydrogen peroxide is used to increase the solubility of the organic compound in the $H_2O_2$ aqueous phase. Examples of suitable solvents include acetone and methanol.

Particular advantages of the present invention are that the process uses mild temperature and pressure conditions and the conversion and yield are high and by-product formation is small. In particular the peroxide conversion is high. The optimum reaction temperature is between 50° and 150° C., preferably about 100° C. when using hydrogen peroxide, the temperature may be higher when using organic peroxides, for example up to 200° C. The pressure should be such that all materials are in the liquid or dense phase.

The reaction can be carried out at room temperature but higher reaction rates may be involved at higher temperatures, for example under reflux conditions. Through increase of the pressure either due to the autogeneous pressure created by the heated reactants or by use of a pressurised reactor still higher temperatures can be reached. Use of higher pressures in the range of 1 to 100 bars ($10^5$ to $10^7$ Pa) can increase the conversion and selectivity of the reaction.

The oxidation reaction can be carried out under batch conditions or in a fixed bed, and the use of the heterogeneous catalyst enables a continuous reaction in a monophase or biphase system. The catalyst is stable under the reaction conditions, and can be totally recovered and reused.

The process of the present invention is preferably carried out in the presence of a solvent. Choice of solvent is important since it should dissolve the organic phase and the aqueous phase when hydrogen peroxide is used which is generally present due to the use of aqueous hydrogen peroxide as the oxidising agent, where organic hydroperoxides are used suitable organic solvents should be used. Polar compounds are preferred which are inert under reaction conditions, and examples of preferred solvents are alcohols, ketones and ethers, with a number of carbon atoms which is not too high, preferably less than or equal to 6. Methanol or tertiary butanol is the most preferred of the alcohols, acetone and butanone are the most preferred of the ketones. The amount of solvent is important and can influence the reaction product and the conversion, the choice of solvent and the amount depending on the material to be oxidised for example we have found that when oxidising normal hexane with aqueous hydrogen peroxide yields are improved when the ratio of acetone to hexane is in the range 1:1 to 4:1. The solvent improves the miscibility of the hydrocarbon phase and the aqueous phase which is generally present due to the use of aqueous hydrogen peroxide as the oxidising agent. If, however, the peroxide is supplied as a solution, such as tertiary butyl hydroperoxide which is frequently dissolved in ditertiary butyl peroxide, and the substrate is soluble in the solvent then no additional solvent is required.

The invention will be described with further details including a preparation of the catalyst and several examples of oxidation reactions.

EXAMPLES

Example 1

Synthesis of Titanium Containing Zeolite Beta

Six samples of titanium containing zeolite Beta were synthesized from synthesis mixtures with the following molar compositions.

TABLE 1

| | Molar Compositions of the Synthesis Mixtures | | | | | |
|---|---|---|---|---|---|---|
| Sample | TiBeta1 | TiBeta2 | TiBeta3 | TiBeta4 | TiBeta5 | TiBeta6 |
| $SiO_2$ | 1 | 1 | 1 | 1 | 1 | 1 |
| $TiO_2$ | 0.0286 | 0.0284 | 0.0859 | 0.1718 | 0.0284 | 0.0855 |
| $Al_2O_3$ | 0.0069 | 0.0074 | 0.0070 | 0.0072 | 0.0200 | 0.0200 |
| TEAOH | 0.9576 | 0.9628 | 0.9580 | 0.9580 | 0.9369 | 0.9176 |
| $H_2O$ | 79.25 | 80.17 | 80.18 | 80.96 | 78.77 | 77.92 |

Tetraethylorthotitanate (TEOT) was used as a source of $TiO_2$

Ludox AS40 (40% colloidal silica, Du Pont) was used as a source of $SiO_2$ Al powder was used as a source of $Al_2O_3$.

The synthesis mixtures were prepared as follows:

The required amount of TEOT was added to water and then cooled to 5° C. To the resulting white suspension, precooled $H_2O_2$ (35 wt. % in water) was added so that a yellow solution was obtained.

The following amounts of $H_2O_2$ were used.

| | TiBeta1 | TiBeta2 | TiBeta3 | TiBeta4 | TiBeta5 | TiBeta6 |
|---|---|---|---|---|---|---|
| $H_2O_2$:TEOT Ratio | 95 | 185 | 62 | 31 | 185 | 62 |

This solution was kept stirring at 5° C. during 3 hours. The required amounts of Al powder and tetraethylammoniumhydroxide (TEAOH) (40% in water) were mixed and heated to 80° C. during 3 hours in order to dissolve the Al powder. The water was added and the solution cooled to 5° C.

The Ti and Al containing solutions were mixed and kept stirred at 5° C. for 1 hour. Then the required amount of Ludox AS40 was added and the mixture kept at room temperature for 18 hours. It was then heated to 70° C. for 2 hours and cooled to room temperature again.

After addition of some ethanol (±10 ml per 175 ml synthesis mixture), the mixture was transferred to a stainless steel autoclave with a volume of 130 ml. The autoclave was kept at 135° C. for 6 days. For the synthesis of TiBeta samples, 1, 2, 3 and 6 the autoclave was static, for the synthesis of TiBeta 4 and 5 the autoclaves were rotated. After 6 days (10 days for sample TiBeta 3), the autoclave was cooled, the solid material contained in it was separated from the mother liquor, washed with water by subsequent centrifugations, and dried at 60° C.

Finally the samples were calcined at 550° C. in air for 12 hours.

All samples were characterized by an IR absorption band at around ±960 $cm^{-1}$.

Example 2

Oxidation of n-hexane by $H_2O_2$

TiBeta samples 1, 2 and 5 prepared in Example 1 were used as catalysts for the oxidation of n-hexane by $H_2O_2$. The catalysts were either used as such or after treatment with inorganic acids, bases or steam. The reactions were carried out at 100° C. using the conditions specified in Table 2. The observed n-hexane conversions and product selectivities are listed in Table 2. Acetone was used as solvent except in Experiment 2 which used methanol.

The results show that all samples catalyze the oxidation of n-hexane to 2- and 3-hexanols and hexanones. Comparison of the conversion obtained in experiment No. 3 with that obtained in experiment No. 1 shows that the oxygenation activity of the catalysts in this reaction can be improved significantly by treating them with acids or bases. The high conversion obtained in experiment No. 7 shows that steaming of the catalyst also has a positive effect on their oxygenation activity.

Example 3

Oxidation of Cyclohexane by $H_2O_2$

TiBeta samples 1, 2, 3 and 6 prepared in example 1 were used as catalysts for the oxidation of cyclohexane by $H_2O_2$. The catalysts were either used as such or after treatment with acids, bases or steam. For comparison, two existing catalysts TS-1 (synthesized according to the procedure described in example 2 of U.S. Pat. No. 4,410,501) and TiBeta (synthesized according to the procedure described in J. Chem. Soc. Chem. Comm. 8 (1992), with x=0.023) (Experiment 9 of Table 3), were also tested as catalysts for the oxidation of cyclohexane, surprisingly Experiment 9 produced a very small amount of adipic acid although this is not reported in the article.

The reaction conditions and the observed cyclohexane conversions and product selectivities are listed in Table 3. 2-Butanone was used as solvent for Experiments 4–9 and acetone was used for Experiments 2 and 3. Experiment 1 was solvent free.

TABLE 2

Oxidation of n-Hexane

| | | | Reaction Conditions | | | | | | Product Selectivity (%) | | | |
| | | | Amount | | | | Reaction | Convers. | | | | |
| Exp. No. | Catalyst | Treatment(s)[a] | Catalyst (g) | n-hexane (mmol) | $H_2O_2$[b] (mmol) | Amount Solvent | Time (hrs) | n-hexane (%) | 2-hexanol | 3-hexanol | 2-hexanone | 3-hexanone |
|---|---|---|---|---|---|---|---|---|---|---|---|---|
| 1 | TiBeta1 | / | 0.20 | 117 | 234 | 45 ml | 16 | 2.7 | 25 | 23 | 30 | 22 |
| 2 | TiBeta1 | $NH_3$/Na/C | 0.23 | 119 | 226 | 45 ml | 22 | 2.3 | 27 | 27 | 27 | 19 |
| 3 | TiBeta1 | $NH_3$/Na/C/A/C | 0.07 | 117 | 280 | 45 ml | 22 | 6.9 | 24 | 27 | 25 | 24 |
| 4 | TiBeta2 | A/C | 0.54 | 118 | 234 | 45 ml | 23 | 8.2 | 20 | 16 | 33 | 31 |
| 5 | TiBeta5 | A/C | 0.50 | 113 | 230 | 34 g | 22 | 6.7 | 13 | 11 | 42 | 34 |
| 6 | TiBeta5 | A/C/S/A/C | 0.11 | 113 | 230 | 34 g | 22 | 9.9 | 18 | 15 | 34 | 33 |
| 7 | TiBeta5 | Ss | 0.50 | 113 | 230 | 34 g | 22 | 10.3 | 20 | 16 | 36 | 28 |
| 8 | TiBeta5 | Ss/A/C | 0.50 | 113 | 230 | 34 g | 22 | 9.0 | 14 | 12 | 40 | 34 |

[a]Treatments are carried out subsequently:
$NH_3$: catalyst is put in as an aqueous $NH_3$ solution of pH 11.8 at room temperature during ½ hour, recovered by centrifugation and washed with distilled water.
Na: catalyst is put in a 0.056 wt % solution of NaCl in water at room temperature during 20 hours, recovered by centrifugation and washed with distilled water.
C: calcination at 550° C. under air.
A: catalyst is put in a 1.3 HCl solution at reflux temperature during 3 hours, recovered by centrifugation and washed with distilled water.
S: catalyst is contacted with water until incipient wetness, and heated at 550° C. during 1 hour in a covered crucible.
Ss: catalyst is heated at 700° C. under $N_2$ flow and a water flow of ±50 ml water/g catalyst, hr is brought through the catalyst bed during 1 hour.
[b]A 35% solution of $H_2O_2$ in water was used.

TABLE 3

Oxidation of Cyclohexane

| | | | | | | | Reaction Time (hrs) | Reaction Temp (°C.) | Convers. Cyclohexane (%) | Product Selectivity (%) | | | | |
|---|---|---|---|---|---|---|---|---|---|---|---|---|---|---|
| Exp. No. | Catalyst | Treatment(s)[a] | Amount Catalyst (g) | Cyclohexane (mmol) | $H_2O_2$[b] (mmol) | Amount Solvent | | | | Cyclohexanol | Cyclohexanone | Cyclohexanediols | Cyclohexanediones | Adipic Acid (%) |
| 1 | TiBeta1 | $NH_3$/Na/A/C | 0.21 | 136 | 230 | 0 | 1 | 94 | 0 | / | / | / | / | / |
| 2 | TiBeta2 | $NH_3$/Na/A/C | 0.11 | 143 | 214 | 20 ml | 3 | 94 | 2.5 | 44 | 56 | / | / | / |
| 3 | TiBeta2 | A/C | 0.34 | 139 | 238 | 45 ml | 22 | 97 | 7.6 | 33 | 67 | / | / | / |
| 4 | TiBeta2 | A/C | 0.18 | 32 | 94 | 56 g | 4 | 97 | 25.8 | 7.1 | 12.5 | 0.8 | 23.2 | 1.6 |
| 5 | TiBeta3 | / | 0.20 | 33 | 94 | 56 ml | 16 | 97 | 28.0 | 16.9 | 0 | 21.4 | 2.2 | 4.3 |
| 6 | TiBeta3 | $NH_3$/Na/C/A/C | 0.07 | 33 | 94 | 56 ml | 4 | 96 | 47.0 | 0.8 | 4.0 | 12.0 | 4.1 | 54.0 |
| 7 | TiBeta6 | / | 0.20 | 33 | 94 | 56 g | 4 | 100 | 16.7 | 10.8 | 13.9 | 46.7 | 16.3 | 2.7 |
| 8 | TS-1[c] | / | 0.20 | 33 | 94 | 56 g | 4 | 96 | 16.0 | 20.1 | 8.9 | / | 22.6 | / |
| 9 | TiBeta | / | 0.20 | 33 | 94 | 56 g | 4 | 97 | 19.0 | 5.4 | 9.1 | 77.4 | 7.0 | 1.1 |

[a]Treatments are carried out subsequently:
$NH_3$: catalyst is put in as an aqueous $NH_3$ solution of pH 11.8 at room temperature during ½ hour, recovered by centrifugation and washed with distilled water.
Na: catalyst is put in a 0.056 wt % solution of NaCl in water at room temperature during 20 hours, recovered by centrifugation and washed with distilled water.
C: calcination at 550° C. under air.
A: catalyst is put in a 1.3 HCl solution at reflux temperature during 3 hours, recovered by centrifugation and washed with distilled water.
S: catalyst is contacted with water until incipient wetness, and heated at 550° C. during 1 hour in a covered crucible.
Ss: catalyst is heated at 700° C. under $N_2$ flow and a water flow of ±50 ml water/g catalyst, hr is brought through the catalyst bed during 1 hour.
[b]A 35% solution of $H_2O_2$ in water was used.
[c]Comparative.

The data illustrates that in the presence of a solvent all catalysts are active for the oxidation of cyclohexane by $H_2O_2$, with formation of cyclohexanol and cyclohexanone. In acetone, these are the only observed oxidation products in 2-butanone however, cyclohexanediols, cyclohexanedions and adipic acid are also observed upon oxidation of cyclohexane. In experiment No. 6 adipic acid is even the main oxidation product. On the comparative catalyst TS-1 however, no formation of adipic acid occurs under comparable reaction conditions.

Comparison of the cyclohexane conversions obtained in experiments 6 and 7 shows again that the oxygenation activity of titanium containing zeolites Beta is greatly improved by treatment of the catalysts with acids or bases.

Example 4

The process of the present invention was compared with that described in the Journal Chem. Soc. Chem. Commun. 1992 (8) 589–590 with the following results. This shows that the latter has a lower activity and does not produce adipic acid under identical experimental conditions.

TABLE 4

Oxidation of Cyclohexane with T-BuOOH as the Oxidant in the Presence of Tiβ and the Catalyst Synthesised as Described in J. Chem. Soc.

| | Tiβ | J. Chem. Soc. |
|---|---|---|
| Reaction Conditions (stirred batch) | | |
| Catalyst (wt %) | 2 | 2 |
| t-BuOOH/Cyclohexane (mol/mol) | 2.4 | 2.4 |
| Solvent | 0 | 0 |
| Time (h) | 4 | 4 |
| Temperature (°C.) | 100 | 100 |
| Results - Mole % | | |
| Cyclohexane Conversion Selectivity | 35 | 16 |

TABLE 4-continued

Oxidation of Cyclohexane with T-BuOOH as the Oxidant in the Presence of Tiβ and the Catalyst Synthesised as Described in J. Chem. Soc.

| | Tiβ | J. Chem. Soc. |
|---|---|---|
| Cyclohexanol | 15 | 2 |
| Cyclohexanone | 4 | 2 |
| 1,4-cyclohexanedione | 0 | 27 |
| Adipic Acid | 77 | 0 |
| Others | 4 | 69 |

Example 5

The process of the present invention was used to oxidise 1-octanol.

TABLE 5

Oxidation of 1-Octanol with Tiβ and tBuOOH to the Corresponding Acid: Octanoic Acid

| Reaction Conditions: | |
|---|---|
| Catalyst (wt %) | 2 |
| tBuOOH/1C$_8$OH (mole/mole) | 1:1 |
| Solvent | none |
| Time (h) | 4 |
| Temperature °C. | 100 |
| The following was obtained: | |
| Conversion (%) mole | 50 |
| Octanoic Acid (%) mole | 75 |
| Octanal (%) mole | 7 |
| Unknowns (%) mole | 18 |

Example 5 of EP 0102655 A2 shows that when using TS-1 as the catalyst and $H_2O_2$ as the oxidant no octanoic acid is formed.

Example 6

The process of the present invention is used to oxidise cyclopentane with hydrogen peroxide and was compared with the yield using TS-1 as catalyst.

TABLE 6

Oxidation of Cyclopentane with Hydrogen Peroxide in the Presence of Tiβ and TS-1 Respectively

|  | Tiβ | TS-1 |
|---|---|---|
| Reaction Conditions (stirred batch): | | |
| Catalyst (wt %) | 6.7 | 6.4 |
| Cyclopentane (mmol) | 40 | 42 |
| $H_2O_2$ (mmol) | 94 | 96 |
| Acetone (g) | 45 | 45 |
| Reaction time (h) | 24 | 24 |
| Results - mole %: | | |
| Cyclopentane Conversion | 50 | 36 |
| Selectivity: | | |
| Cyclopentanol and Cyclopentanone | 34 | 60 |
| Glutaric Acid | 37 | 8 |
| Others | 29 | 32 |

BRIEF DESCRIPTION OF THE DRAWINGS

The Diffuse Reflectance Spectroscopy traces for the titanium Beta (a) of the invention and the product synthesis according to the Journal of the Chemical Society (b) are shown in FIG. 1 and the Infra Red Spectra are shown in Figure 2.

Example 7

Oxidation of Toluene

Figure 1:
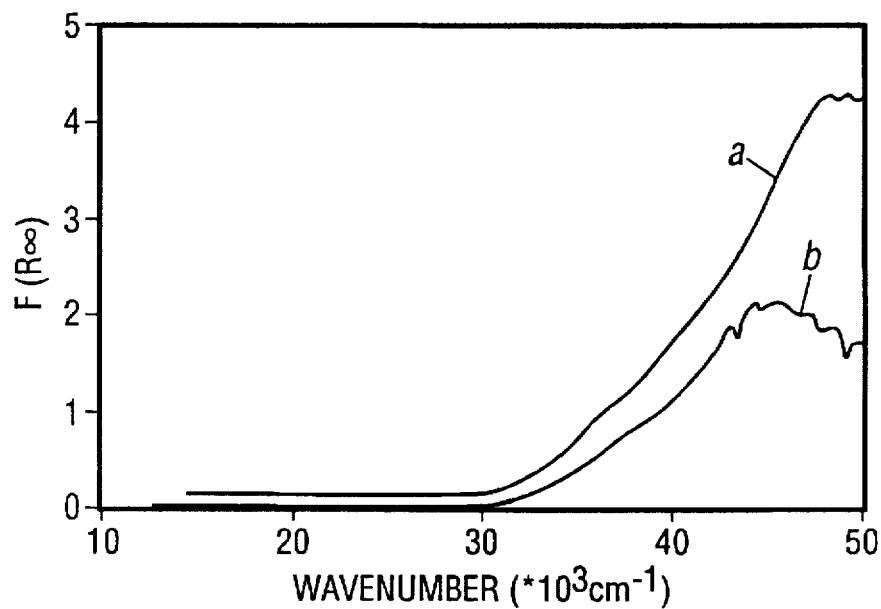
Figure 2:
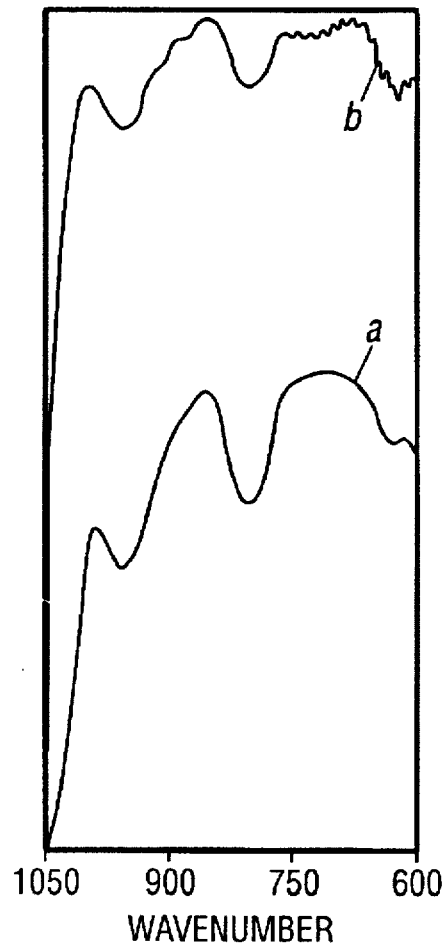

The process of the present invention was used to oxidise toluene.

TABLE 7

Oxidation of Toluene in the Presence of Ti-β/t-BuOOH

| Reaction Conditions: | |
|---|---|
| Catalyst (wt %) | 0.73 |
| t-BuOOH/toluene (mole/mole) | 1.70 |
| Solvent | none |
| Time (h) | 4 |

TABLE 7-continued

Oxidation of Toluene in the Presence of Ti-β/t-BuOOH

| Temperature (°C.) | 104 |
|---|---|
| Results - mole %: | |
| Toluene conversion | 25 |
| Selectivity - mole %: | |
| Benzylalcohol | 21 |
| Benzaldehyde | 34 |
| Benzoic acid | 21 |
| Phenol | 6 |
| o-cresol | 0.8 |
| p-cresol | 3 |
| Unknowns | 14.2 |

Example 8

Various catalysts were prepared using the conditions set out in Table 7 and their properties were found to be as set out in Table 8.

TABLE 8

| Synthesis Code | Gel Composition (molar ratios) | | | | | Evap. time at 70° C. (h) | Crystallization Conditions | | |
|---|---|---|---|---|---|---|---|---|---|
| | $SiO_2/TiO_2$ | $SiO_2/Al_2O_3$ | $OH^-/SiO_2$ | $EtOH/SiO_2$ | $H_2O/SiO_2$[a] | | Head-space (°C.) | Temp (°C.) | Time (days) |
| 10 | ∞ | 31 | 0.52 | 0 | 12 | 0 | 12 | 125 | 6 |
| 11 | 26 | 31 | 0.52 | 1 | 12 | 0 | 12 | 125 | 6 |
| 12 | 5 | 143 | 0.94 | 2 | 95 | 0 | 40 | 150 | 7 |
| 13 | 5 | 147 | 0.95 | 2 | 98 | 4 | 33 | 125 | 6 |
| 14 | 35 | 145 | 0.96 | 2 | 98 | 2 | 50 | 125 | 6 |
| 15 | 12 | 143 | 0.96 | 2 | 99 (42) | 2 | 50 | 135 | 10 |
| 16 | 12 | 50 | 0.96 | 2 | 100 (25) | 2 | 50 | 135 | 10 |
| 17 | 18 | 142 | 0.98 | 1 | 40 (25) | 2.5 | 5 | 140 | 11 |
| 18 | 18 | 142 | 0.98 | 1 | 40 (25) | 2.5 | 5 | 140 | 13 |
| 19 | ∞ | 143 | 0.98 | 1 | 42 (28) | 2.5 | 5 | 140 | 11 |
| 20 | 38 | 385 | 0.55 | 0 | 22 | 0 | 50 | 135 | 10[b] |

[a]$H_2O/SiO_2$: Values between brackets indicate the $H_2O/SiO_2$ ratio after evaporation.
[b]Agitation is used at 50 rpm.

| | | | | IR | | | DRS | | |
|---|---|---|---|---|---|---|---|---|---|
| Synthesis Code | Remarks | Yield (%) | XRD | 960 cm$^{-1}$ | 575 cm$^{-1}$ | 525 cm$^{-1}$ | 30,800 cm$^{-1}$ | 34,000 cm$^{-1}$ | 47,500 cm$^{-1}$ |
| 10 | NaOH added | 35 | β | no | yes (s) | yes (s) | no | no | no |
| 11 | NaOH added | 35 | Tiβ | no | yes (s) | yes (s) | yes (s) | yes (s) | no |
| 12 | Ludox HS40/H$_2$O$_2$/no aging | 0 | amorphous | no | no | no | yes (s) | yes (s) | no |
| 13 | Ludox HS40/H$_2$O$_2$/aging | 4 | Tiβ | yes (w) | yes (s) | yes (s) | yes (vw) | yes (w) | yes (s) |
| 14 | Ludox AS40/H$_2$O$_2$/aging | 20 | Tiβ | yes (s) | yes (s) | yes (s) | no | no | yes (s) |
| 15 | more Ti/increased time and temp. | 35 | Tiβ | yes (s) | yes (s) | yes (s) | no | no | yes (s) |
| 16 | more Al | 75 | Tiβ | yes (s) | yes (s) | yes (s) | no | yes (s) | yes (s) |
| 17 | small head-space | 55 | Tiβ | yes (s) | yes (s) | yes (s) | no | no | yes (s) |
| 18 | large head-space/high ethylene pressure | 55 | Tiβ | yes (s) | yes (s) | yes (s) | no | no | yes (s) |
| 19 | no Ti | 42 | β | no | yes (s) | yes (s) | no | no | no |
| 20 | | 10 | J. Chem. Soc. 589 (1992) | yes (vw) | yes (s) | yes (s) | yes (w) | yes (s) | no |

Yield (%): The synthesis yields is defined as $\frac{\text{weight of calcined zeolite obtained}}{\text{weight of SiO}_2 + \text{Al}_2\text{O}_3 \text{ in the gel}} * 100$ XRD: Crystalline phase obtained.

IR: The bands at 575 and 525 cm$^{-1}$ are typical zeolite Beta framework vibrations; the band at 960 cm$^{-1}$ is assigned to Ti = 0 vibrations. Indications between bracket (arbitrary): vw = very weak; w = weak and s = strong.

DRS: The band around 30,800 cm$^{-1}$ is assigned to agglomerated TiO$_2$ (e.g. anatase);
34,000 cm$^{-1}$ finely dispersed TiO$_2$;
47,500 cm$^{-1}$ isolated titanium.

These results again show the difference between the titanium Beta of the invention (11 to 18) with zeolite Beta (10 and 19) and the titanium Beta synthesised according to the Journal of the Society of Chemistry Comm. 8 (1992) (synthesis 20).

We Claim:

1. A process for the preparation of a titanium-containing zeolite beta from a synthesis mixture comprising a hydrolyzable source of titanium, a source of silicon, a source of aluminum and an organic, nitrogen-containing base, said process comprising, mixing said source of titanium, said source of aluminum and said source of silicon, to form crystals of titanium-containing zeolite beta, wherin said source of titanium is at least partially hydrolyzed.

2. The process of claim 1 wherein said zeolite beta is prepared in the presence of hydrogen peroxide to at least partially hydrolyze said source of titanium, and provide a synthesis mixture that yields titanium containing zeolite beta that has the following molar composition.

| SiO$_2$ | (0.0001–0.2) TiO$_2$ | (0.005–0.100) Al$_2$O$_3$ |
|---|---|---|
| | (10–100) H$_2$O | (0.1–1) TEAOH. |

3. The process of claim 2 wherein the molar ratio of titanium and silicon to aluminium in the synthesis mixture is in the range from 10 to 200.

4. The process of claim 2 wherein the hydrogen peroxide is present in an amount which provides 10 to 200 moles per mole of TEOT and TEOT is used as the source of titanium.

5. The process of claim 1 wherein said titanium-containing zeolite beta is contacted with an inorganic base, inorganic acid, ion exchange resin, or steam.

6. The process of claim 5 wherein said zeolite beta is further calcined.

7. A titanium-containing zeolite beta prepared from a synthesis mixture comprising a hydrolyzable source of titanium, a source of silicon, a source of aluminum and an organic, nitrogen-containing base, wherein said source of titanium, said source of aluminum and said source of silicon are mixed in the presence of said base to form crystals of said titanium-containing zeolite beta, and wherein said source of titanium is at least partially hydrolyzed.

8. A process comprising the oxidation of organic compounds with the titanium-containing zeolite beta of claim 7.

9. The process of claim 8 wherein said oxidation is carried out in the presence of organic hydroperoxides or N$_2$O.

10. The process of claim 9 wherein said organic compound is cyclohexane and an organic hydroperoxide is present.

11. The process of claim 10 further comprising recovering adipic acid.

* * * * *